(12) United States Patent
Valkoun et al.

(10) Patent No.: US 12,357,466 B2
(45) Date of Patent: Jul. 15, 2025

(54) EXPANDABLE INTERBODY SPACER

(71) Applicant: Astura Medical Inc., Irving, TX (US)

(72) Inventors: Anthony Valkoun, Irving, TX (US); Thomas Purcell, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 17/513,843

(22) Filed: Oct. 28, 2021

(65) Prior Publication Data

US 2022/0125596 A1    Apr. 28, 2022

Related U.S. Application Data

(60) Provisional application No. 63/106,876, filed on Oct. 28, 2020.

(51) Int. Cl.
*A61F 2/44* (2006.01)
*A61F 2/30* (2006.01)

(52) U.S. Cl.
CPC .............. *A61F 2/442* (2013.01); *A61F 2/447* (2013.01); *A61F 2002/3055* (2013.01); *A61F 2002/30556* (2013.01); *A61F 2002/30579* (2013.01)

(58) Field of Classification Search
CPC .............. A61F 2/442; A61F 2002/3055; A61F 2002/30556; A61F 2002/30579; A61F 2250/0004–001; A61F 2250/0048; A61F 2/4425–2002/443; A61F 2/4455–2/447; A61B 17/8038; A61B 17/8047
USPC ........................................... 623/17.15, 17.16
See application file for complete search history.

(56) References Cited

U.S. PATENT DOCUMENTS

| | | | |
|---|---|---|---|
| 8,986,387 B1 | 3/2015 | To et al. | |
| 9,730,806 B2 | 8/2017 | Capote | |
| 10,299,934 B2 | 5/2019 | Seifert et al. | |
| 10,980,644 B2 | 4/2021 | Purcell et al. | |
| 2006/0009770 A1* | 1/2006 | Speirs | A61B 17/8047 606/328 |
| 2015/0012097 A1* | 1/2015 | Ibarra | A61F 2/447 623/17.15 |
| 2019/0388232 A1* | 12/2019 | Purcell | A61F 2/4455 |

(Continued)

FOREIGN PATENT DOCUMENTS

WO    WO2017/066226 A1    4/2017

OTHER PUBLICATIONS

International Search Report and Written Opinion in PCT Application No. PCT/US2021/057159 dated Jan. 18, 2022.

*Primary Examiner* — Eduardo C Robert
*Assistant Examiner* — David C Comstock
(74) *Attorney, Agent, or Firm* — Michael R. Shevlin (57) ABSTRACT

An expandable interbody spacer for placement between adjacent vertebrae having two or more upper and lower endplates having compound-angle linear rods coupled to compound-angle bores configured to couple with the compound-angle linear rods a drive means having corresponding compound-angle slots, ramps or rails configured to slidingly engage the compound-angle slots, ramps or rails of the two or more upper and lower endplates, wherein movement of the drive means in a first direction moves the two or more upper and lower endplates away from each other both vertically and horizontally to expand both a height and a width of the expandable interbody spacer from a collapsed state to an expanded state.

16 Claims, 7 Drawing Sheets

(56) References Cited

U.S. PATENT DOCUMENTS

2020/0163775 A1\* 5/2020 Kim .................. A61F 2/447
2021/0137695 A1\* 5/2021 Huang ................ A61F 2/4455

\* cited by examiner

EXPANDABLE INTERBODY SPACER

CROSS-REFERENCE TO RELATED APPLICATIONS

This application claims the benefit of U.S. Provisional Application No. 63/106,876 filed Oct. 28, 2020, which is incorporated herein by reference.

FIELD

The present invention relates generally to the field of surgery, and more specifically, to an expandable intervertebral body fusion device (i.e., "interbody spacer") for placement in intervertebral space between adjacent vertebrae.

BACKGROUND

A spinal disc can become damaged as a result of degeneration, dysfunction, disease and/or trauma. Conservative treatment can include non-operative treatment through exercise and/or pain relievers to deal with the pain. In surgical treatments, interbody spacers may be used between adjacent vertebra, resulting in spinal fusion of the adjacent vertebra. Treatment options include disc removal and replacement using an interbody spacer such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

A fusion is a surgical method wherein two or more vertebrae are joined together (fused) by way of interbody spacers, sometimes with bone grafting, to form a single bone. The current standard of care for interbody fusion requires surgical removal of all or a portion of the intervertebral disc. After removal of the intervertebral disc, the interbody spacer is implanted in the interspace.

Interbody spacers must be inserted into the intervertebral space in the same dimensions as desired to occupy the intervertebral space after the disc is removed. This requires that an opening sufficient to allow the interbody spacer must be created through surrounding tissue to permit the interbody spacer to be inserted into the intervertebral space. In some cases, the intervertebral space may collapse prior to insertion of the interbody spacer. In these cases, additional hardware may be required to increase the intervertebral space prior to insertion of the implant.

In addition, minimally invasive surgical techniques may have been used on the spine. Under minimally invasive techniques, small incisions are done to access the intervertebral space. Through these incisions, discs are removed and an interbody spacer is placed in the intervertebral disc space to restore normal disc height. Minimally invasive spine surgery offers multiple advantages as compared to open surgery. Advantages include: minimal tissue damage, minimal blood loss, smaller incisions and scars, minimal postoperative discomfort, and relative quick recovery time and return to normal function.

Typical expandable interbody spacers utilize angled ramps in conjunction with slots or t-rails and a separate drive screw mechanism to compress the mechanism and force expansion. Expandable interbody spacers are typically limited in expansion capability at smaller footprints due to a limitation of available material, in addition they typically expand in a single plane (I.E. Height). Current expandable implants are typically expensive and difficult to manufacture due to the complexity of the expansion mechanism and the available manufacturing techniques require the size and positional tolerance of these features to be relatively loose to allow for manufacturability. In addition, this type of mechanism limits the available expansion of the interbody spacer due to the amount of material required to house the slots and/or t-rails.

It would be desirable to develop an easy to manufacture expandable interbody spacer that can be inserted into the intervertebral space at a first smaller dimension and once in place, deploy to a second, larger dimension.

SUMMARY

Disclosed is an expandable interbody spacer that is configured to have an initial collapsed state having a first height and first width suitable for being inserted into an intervertebral space defined by a pair of adjacent vertebrae, and a final expanded state having a second height and second width that is greater than the first height. The expandable interbody spacer may be expanded from the initial collapsed state to the expanded state in-situ. The expanded state increases the distance between the adjacent vertebrae and provides support to the adjacent vertebrae while bone fusion occurs and also provides rigid support between the adjacent vertebrae that withstands compressive forces. By inserting the expandable interbody spacer into the intervertebral space in the initial collapsed state, it is possible to perform the surgery percutaneously with minimal disruption to tissues surrounding the surgical site and intervening soft tissue structures.

Increased height expansion for given implant size, width expansion and lordosis change in conjunction with height expansion. Expandable interbody spacers are typically limited in expansion capability at smaller footprints due to a limitation of available material, in addition they typically expand in a single plane (I.E. Height). Also, expandable implants are typically expensive and difficult to manufacture due to the complexity of the expansion mechanism.

DETAILED DESCRIPTION

Figure 1:
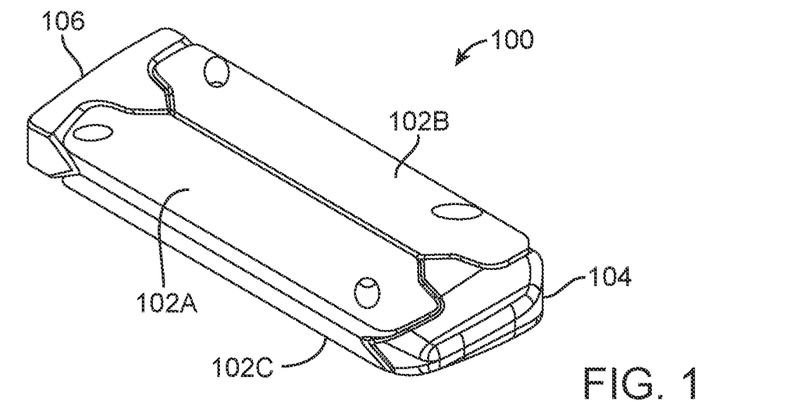
FIG. 1 is a perspective view of an expandable interbody spacer in a collapsed state for introduction into disc space.

The interbody spacer disclosed may be used for anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF). The expandable interbody spacer includes a collapsed state and expanded state. The collapsed state allows insertion between the adjacent vertebrae with minimal dimensions. The expandable interbody spacer expands both vertically and horizontally by means of compound-angle linear rods sliding within compound-angle bores. Upper and lower endplates include compound-angle bores that engage the compound-angle linear rods to move the upper and lower endplates both horizontally and vertically away from each other. The endplates may also be textured to promote bony integration. The compound-angle linear rods have the same compound angle FIG. 1 shows a perspective view of an expandable interbody spacer 100 that consists of 17 primary components, including: a frame, a housing, a threaded rod, a guide rod, a drive screw, 4 endplates, and 8 compound-angle linear rods. The 4 endplates include proximal and distal compound-angle linear rods extending from a top or bottom surface and include proximal and distal compound-angle ramps. At least one of the rods is positioned near a proximal end of the top or bottom surface and least one compound-angle linear rods is positioned near a distal end of the top or bottom surface. The frame and housing both contain compound-angle ramps configured to couple with compound-angle ramps of the top and bottom endplates, and the frame and housing include the compound-angle bores configured to couple with the compound-angle linear rods.

Referring again to FIG. 1. the expandable interbody spacer 100 is shown in a collapsed state having right and left upper endplates 102A, 102B and right and left lower endplates 102C, 102D coupled to a frame 104 and a housing 106. The frame is positioned near a distal end of the expandable interbody spacer 100 and the housing is positioned near a proximal end of the expandable interbody spacer 100.

Figure 2:
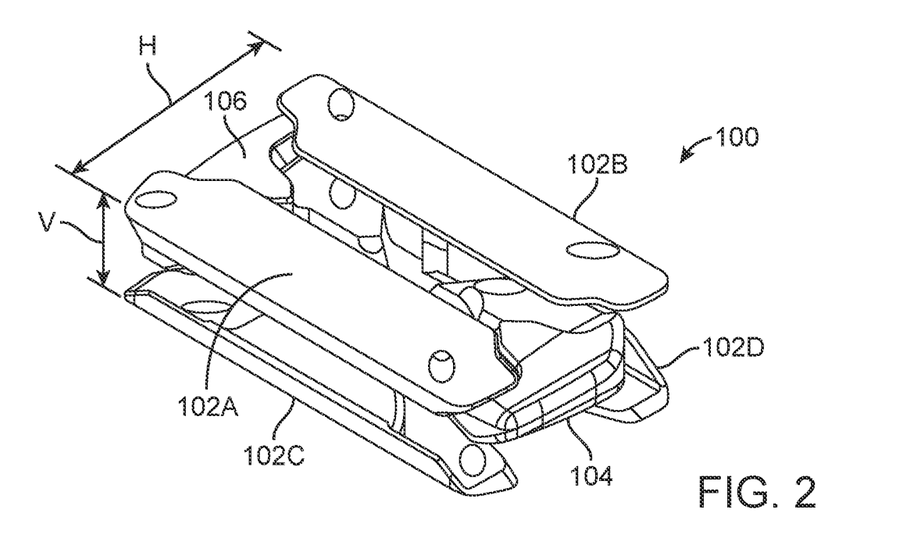
FIG. 2 is a perspective view showing the expandable interbody spacer of FIG. 1 in an expanded state.

FIG. 2 is a perspective view of the expandable interbody spacer 100 in an expanded state with the right upper endplate 102A and left upper endplate 102B expanded vertically V from the right lower endplate 102C and the left lower endplate 102D. The right upper endplate 102A and the right lower endplate 102C are also expanded horizontally H from left upper endplate 102B and left lower endplate 102D.

Figure 3:
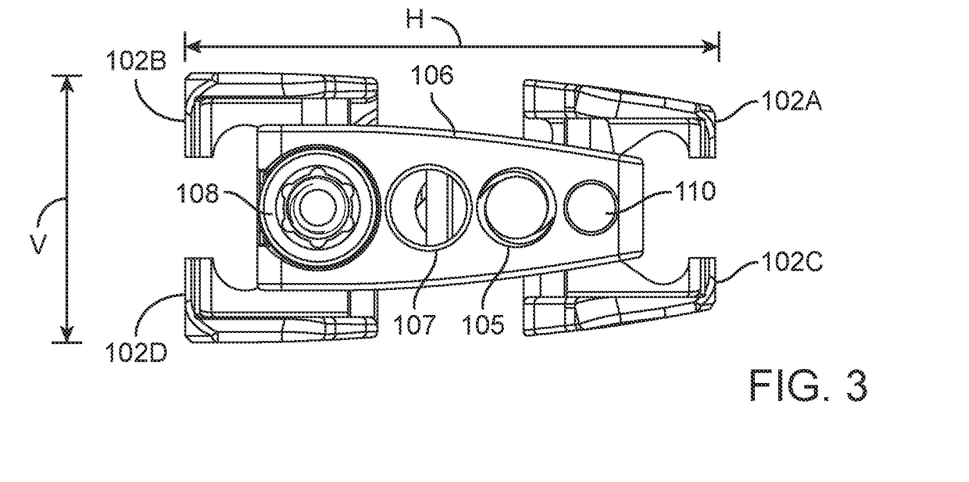
FIG. 3 is a proximal view of the expandable interbody spacer.

FIG. 3 is a proximal view of the expandable interbody spacer 100 with the right and left upper endplates 102A, 102B and the right and left lower endplates 102C, 102D in the expanded state. Also shown is a drive screw 108 and a guide rod 110 coupled to the housing 106. The housing further includes a threaded bore 105 configured to engage a tool for insertion of the expandable interbody spacer 100 and a large bone graft insertion window 107. The housing 106 and frame 104 are positioned relative to each other via the guide rod 110 and a threaded rod 112 coupled with the drive screw 108. Advancing the drive screw 108 causes the housing 106 and frame 104 to translate towards each other. This translation forces multiple compound-angle linear rods 120 housed in the endplates 102A-102D to translate relative to corresponding compound-angle bores 116, facilitating expansion. The drive screw 108 may also include a self-locking mechanism to lock the expandable interbody spacer 100 in a collapsed or expanded state.

In use, when the drive screw is rotated in a first direction the frame 104 and housing 106 move toward each other, moving the right and left upper and lower endplates 102A-102D from the collapsed state to the expanded state. When the drive screw 108 is rotated in a second direction the frame 104 and housing 106 move away from each other, moving the right and left upper and lower endplates 102A-102D from the expanded state to the collapsed state.

Figure 4:
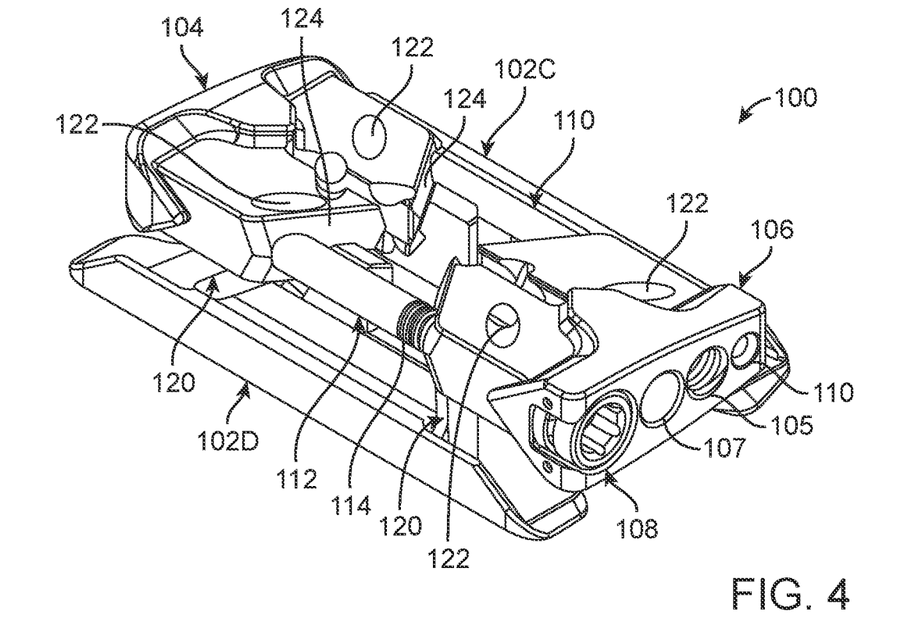
FIG. 4 is an exploded perspective view of the proximal end of the expandable interbody spacer in the expanded state.

FIG. 4 is an exploded perspective view of the proximal end of the expandable interbody spacer 100 in the expanded state, shown without the right and left upper endplates 102A, 102B. In the embodiment shown, the drive mechanism includes a threaded rod 112 having a proximal threaded portion 114 coupled with the drive screw 108 and a distal portion coupled to the frame 104. The guide rod 110 includes a distal end coupled to the frame 104 and a proximal end coupled to the housing 106.

Each of the upper and lower endplates 102A-102D house proximal and distal linear rods 120 at a compound-angle configured to engage compound-angle bores 122 in the frame 104 and housing 106. The distal end of the upper and lower endplates 102A-102D include compound-angle ramps 124 configured to couple compound-angle ramps 126 on the frame 104, and the proximal end of the upper and lower endplates 102A-102D include compound-angle ramps 124 configured to couple compound-angle ramps 126 on the housing 106.

Figure 5:
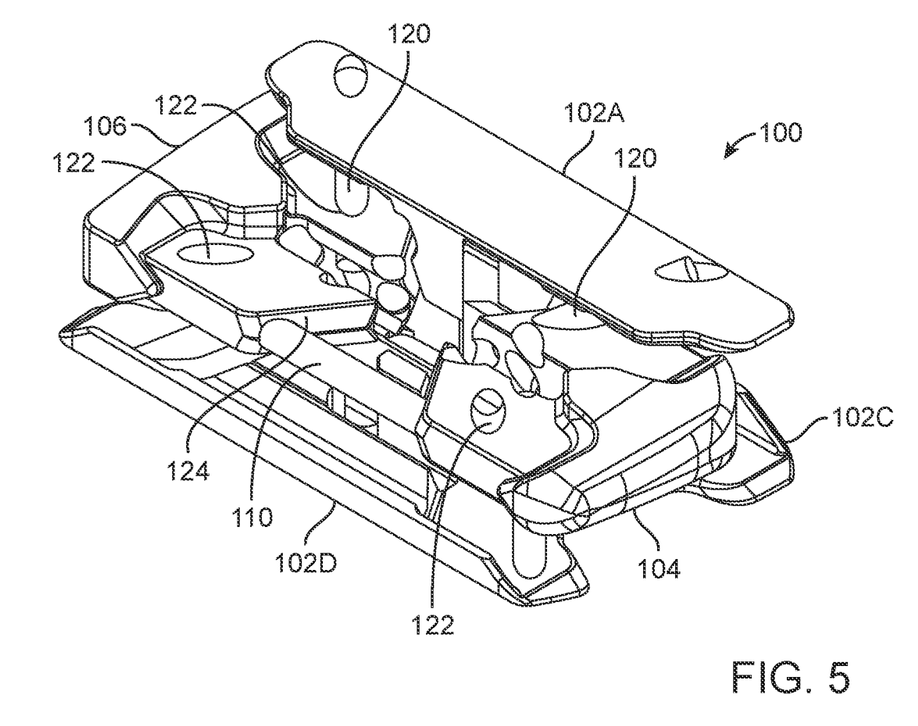
FIG. 5 is an exploded perspective view of the distal end of the expandable interbody spacer in the expanded state.

FIG. 5 is an exploded perspective view of the distal end of the expandable interbody spacer 100 in the expanded state, shown without the upper endplate 102B. In the embodiment shown, the distal end of the guide rod 110 is rigidly coupled to the frame 104 and the proximal end is slidably coupled to the housing 106. Also shown the linear rods 120 engaging the compound-angle bores 122 and the compound-angle ramps 124 on the upper and lower endplates 102A-102D engaging the compound-angle ramps 126 on the frame 104 and housing 106.

As the drive screw 108 is turned in a first direction, the distal frame 104 and proximal housing 106 move closer together. During this movement, the linear rods 120 slide in the compound-angle bores 122, and the compound-angle ramps 124 on the top and bottom endplates 102A-102D engage the compound-angle ramps 126 on the frame 104 and housing 106, to move the upper and lower endplates 102A-102D in the vertical V and horizontal H directions away from each other, expanding the expandable interbody spacer 100.

Figure 6A:
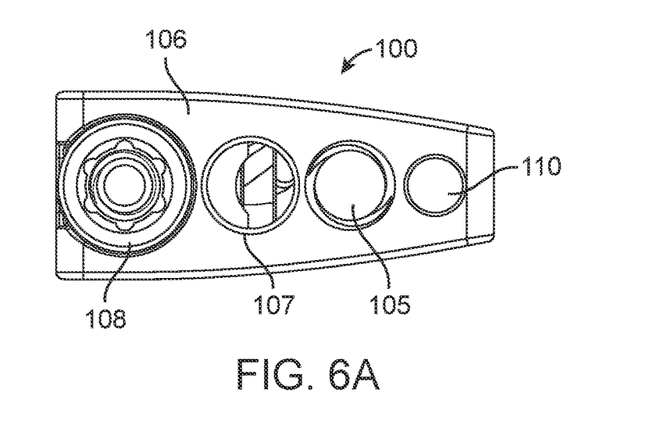
FIGS. 6A-6C show a proximal end view, a side view and a top view of the expandable interbody spacer of FIG. 1 in the collapsed state.

FIG. 6A is a proximal end view of the expandable interbody spacer 100 in the collapsed state showing the housing 106, the drive screw 108, and guide rod 110.

Figure 6B:
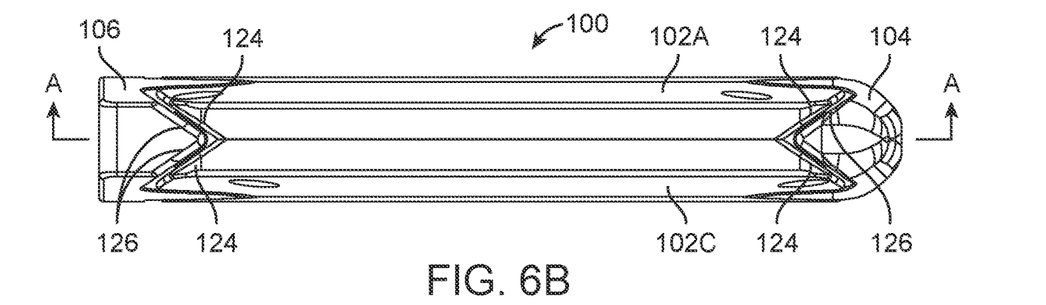

FIG. 6B is a side view of the expandable interbody spacer 100 in the collapsed state showing the upper and lower endplates 102A, 102C, the frame 104 and housing 106. Also shown are the compound-angle ramps 124 on the top and bottom endplates 102A, 102C engaging the compound-angle ramps 126 on the frame 104 and housing 106.

Figure 6C:
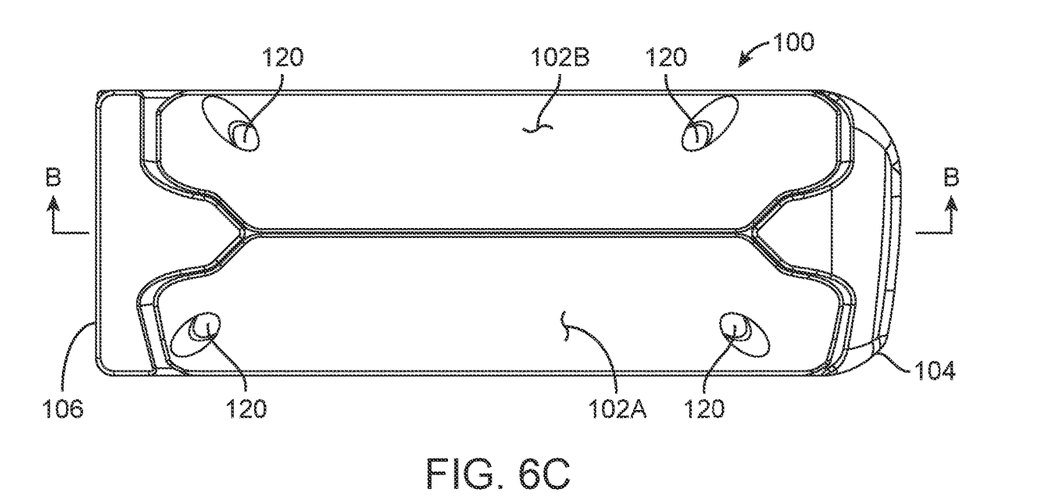

FIG. 6C is a top view of the expandable interbody spacer 100 in the collapsed state showing the upper endplates 102A, 102B and the linear rods 120.

Figure 7:
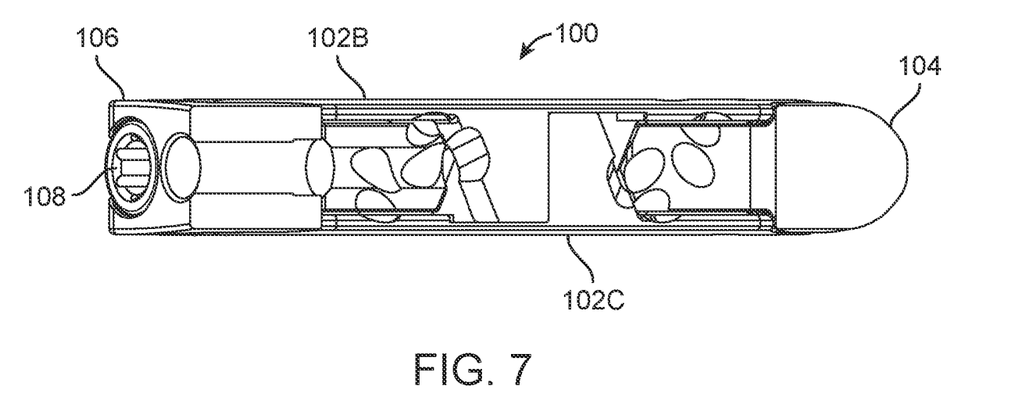
FIG. 7 is a sectional side view at A-A of the expandable interbody spacer.

FIG. 7 is a sectional side view at A-A of the expandable interbody spacer 100 showing the upper and lower endplates 102B, 102D, the frame 104 and housing 106.

Figure 8:
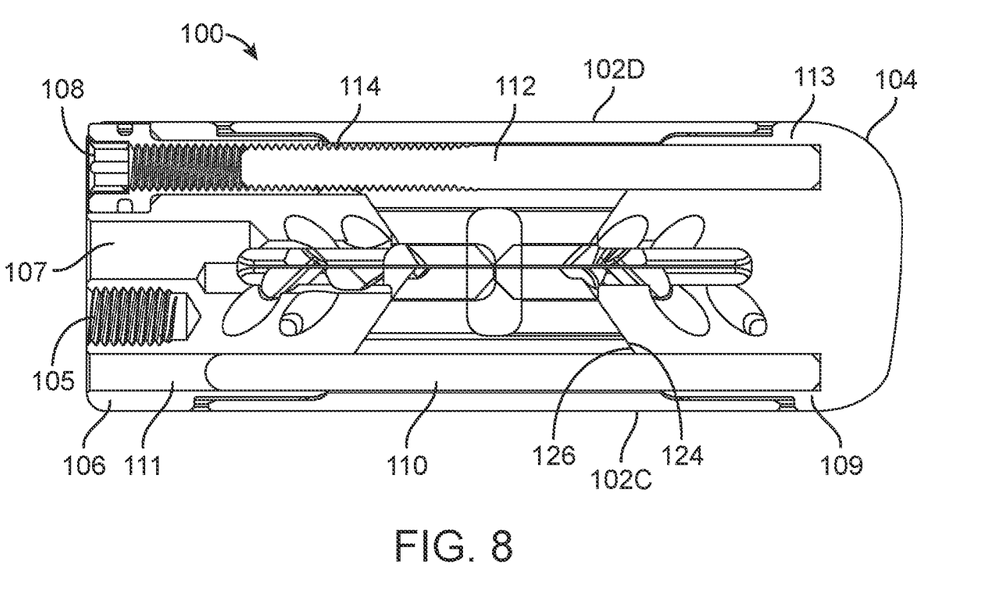
FIG. 8 is a sectional side view at B-B of the expandable interbody spacer.

FIG. 8 is a sectional top view at B-B of the expandable interbody spacer 100 showing the lower endplates 102C, 102D, the frame 104, housing 106. The frame 104 includes a first bore 109 configured to rigidly coupled with the distal end of the guide rod 110. The housing 106 includes a second bore 111 that slidably receives the proximal end of the guide rod 110. The frame 106 includes a third bore 113 configured to rigidly coupled with the distal end of the threaded rod 112. The threads 114 on the proximal end of the threaded rod 112 are configured to couple with the drive screw 108.

Figure 9A:
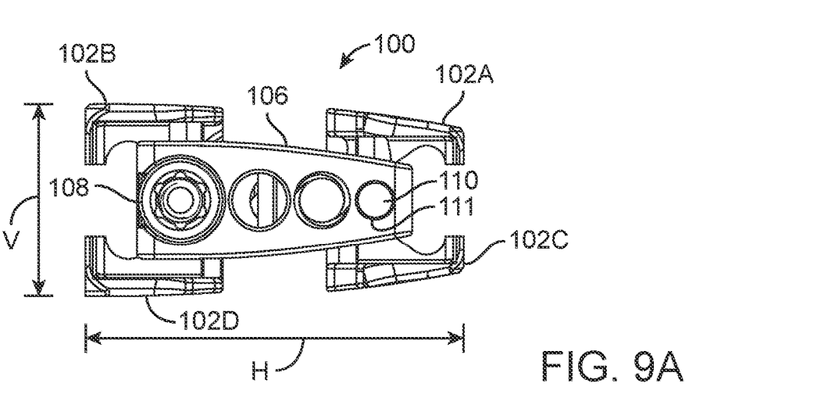
FIGS. 9A-9C show a proximal end view, a side view and a top view of the expandable interbody spacer of FIG. 1 in the expanded state.

FIG. 9A is a proximal end view of the expandable interbody spacer 100 in the expanded state showing the housing 106 with the upper and lower endplates 102A-102D moved in the vertical V and horizontal H directions away from each other, the drive screw 108, and the guide rod 110 within the second bore 111.

Figure 9B:
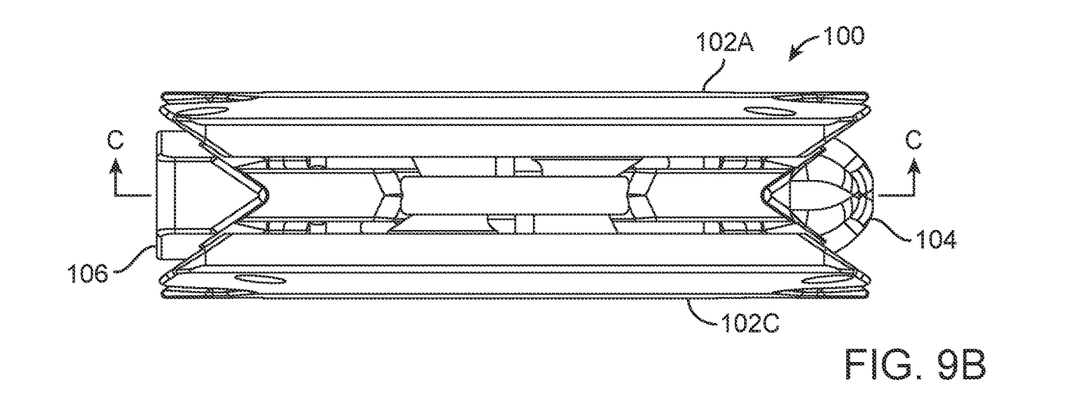

FIG. 9B is a side view of the expandable interbody spacer 100 in the expanded state showing the upper and lower endplates 102A, 102C, the frame 104 and housing 106. Also shown are the compound-angle ramps 124 on the top and bottom endplates 102A, 102C engaging the compound-angle ramps 126 on the frame 104 and housing 106.

Figure 9C:
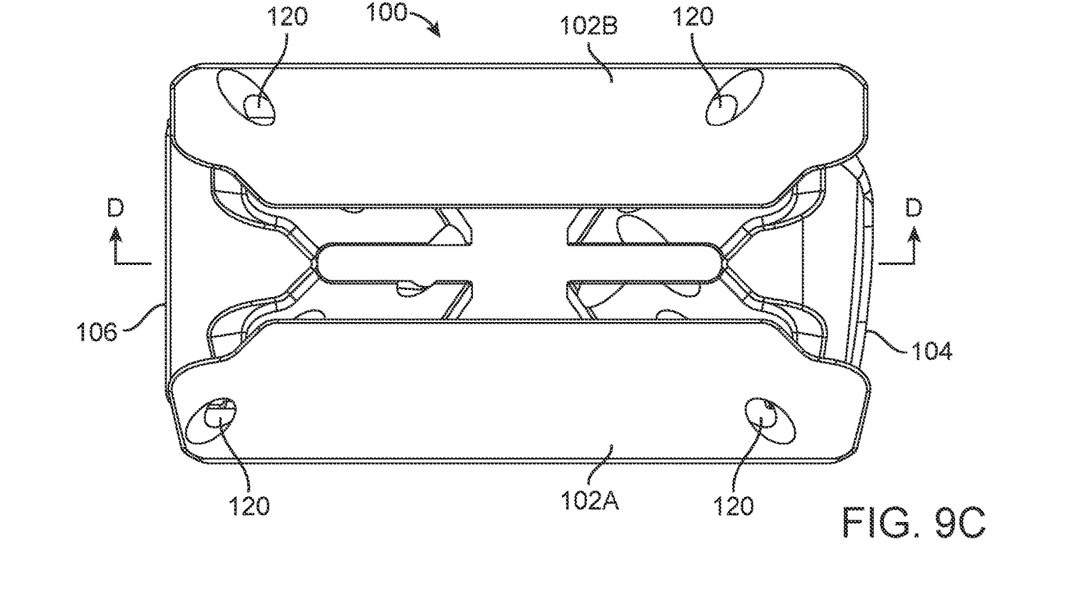

FIG. 9C is a top view of the expandable interbody spacer 100 in the expanded state showing the upper endplates 102A, 102B, the frame 104 and housing 106 and the linear rods 120.

Figure 10:
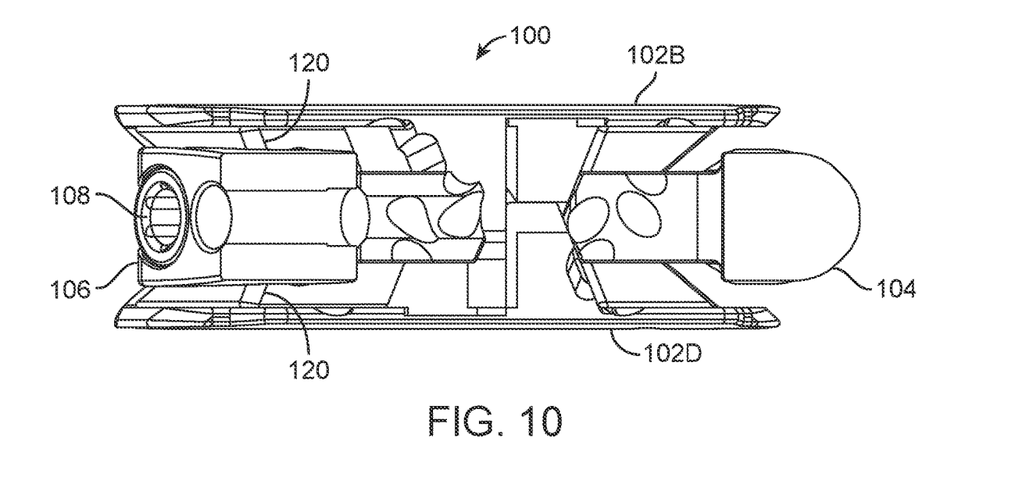
FIG. 10 is a sectional side view at C-C of the expandable interbody spacer.

FIG. 10 is a sectional side view at C-C of the expandable interbody spacer 100 showing the upper and lower endplates 102B, 102D in the expanded position, the frame 104 and housing 106.

Figure 11:
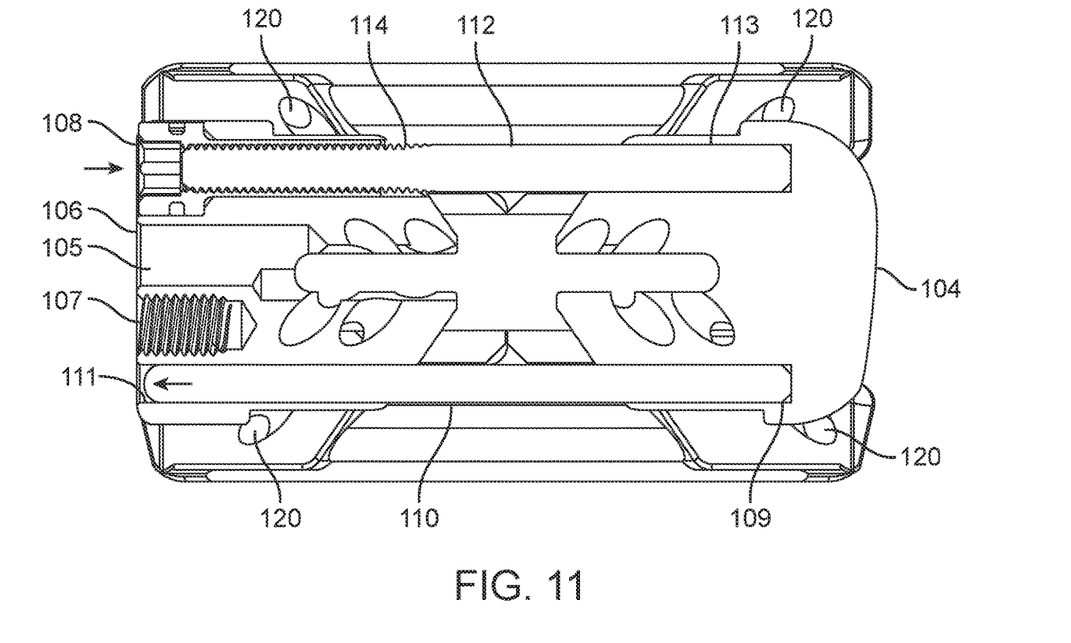
FIG. 11 is a sectional side view at D-D of the expandable interbody spacer.

FIG. 11 is a sectional top view at D-D of the expandable interbody spacer 100 showing the lower endplates 102C, 102D in the expanded state, the frame 104, housing 106. The first bore 109 of the frame 104 is rigidly coupled with the distal end of the guide rod 110. The second bore 111 in the housing 106 is slidably coupled with the proximal end of the guide rod 110. The third bore 113 in the frame 104 is rigidly coupled with the distal end of the threaded rod 112. The threads 114 on the proximal end of the threaded rod 112 are couple with the drive screw 108.

While a drive screw is shown, the drive mechanism can be any mechanism capable of moving the frame and housing away from each other or toward each other to expand or collapse the expandable interbody spacer. Other types of drive mechanisms may include: a belt drive, rack and pinion drive, linear motor drive, ball screw drive, lead screw drive, or any other suitable drive.

While two upper endplates and two lower endplates are in the embodiment shown, other embodiments may include two or more upper endplates and two or more lower endplates. For example, there may be three upper and lower endplates, four upper and lower endplates, etc.

Figure 12A:
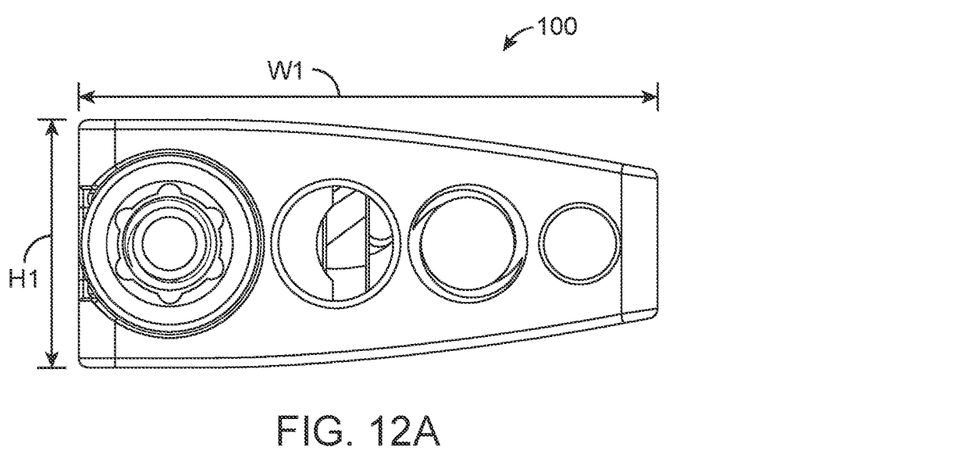
FIGS. 12A and 12B are proximal or front views of the expandable interbody spacer in collapsed and expanded states.
Figure 12B:
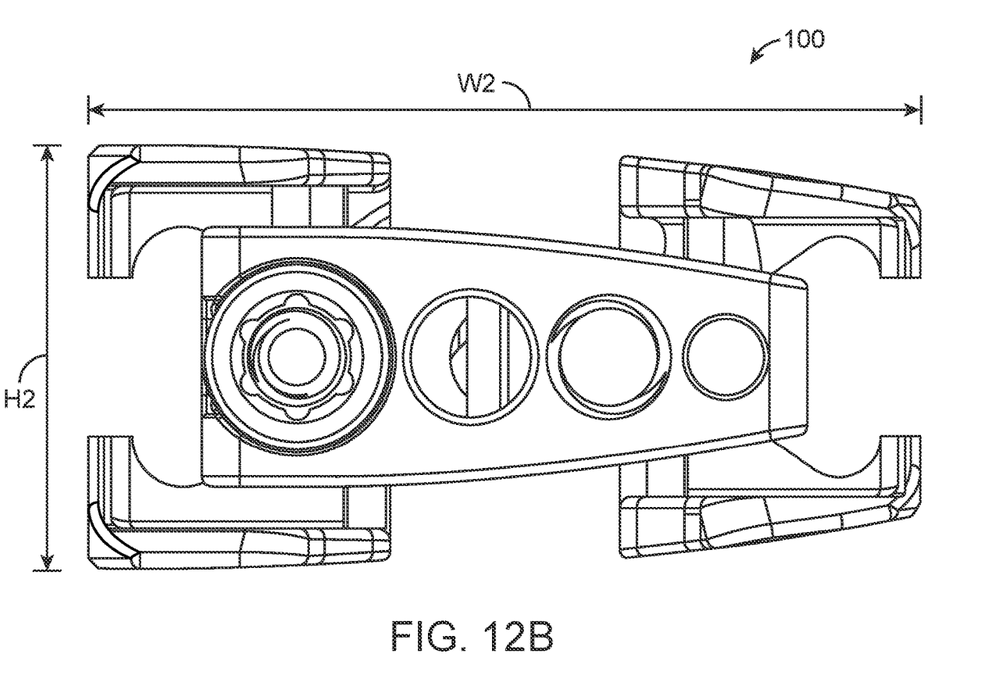

FIGS. 12A and 12B are proximal or front views of the expandable interbody spacer 100 in collapsed and expanded states. When the drive screw 108 is turned or rotated in the first direction, the frame 104 and housing 106 move toward each other and closer together, which moves the upper and lower endplates 102A-102D away from each other both vertically V and horizontally H to expand the expandable interbody spacer 100. During this movement, the linear rods 120 move in the compound-angle bores 122 and the compound-angle ramps 124 on the top and bottom endplates 102A-102D engage the compound-angle ramps 126 on the frame 104 and housing 106 to move the upper and lower endplates 102A-102D.

The design of the compound-angle bores and ramps between the components allow the upper endplates 102A-102B to vertically move V and horizontally move away from the lower endplates 102C-102D, thereby expanding the expandable interbody spacer 100 both vertically and horizontally from the collapsed state (FIG. 12A) to the expanded state (FIG. 12B).

In the collapsed state the expandable interbody spacer 100 has a first height H1 and first width W1. When the screw 108 is rotated in a first direction, the frame 104 and housing 106 start moving toward each other and the endplates expand to a second height H2 and second width W2. The expandable interbody spacer 100 does not have to be completely extended to H2 and can be stopped anywhere between H1 and H2, depending on the expansion needed between the adjacent vertebrae.

In the expanded state the expandable interbody spacer 100 includes a central opening that may be filled with materials, such as bone graft, allograft, Demineralized Bone Matrix ("DBM") or other suitable materials. To insert the materials, the graft insertion window 105 is sized to allow materials to be introduced into the central opening of expandable interbody spacer 100 once is place in desired position.

The upper and lower endplates 102A-102D may include surface features or treatment configured to promote bone growth that engage the bone. For example, the surface may be a textured surface or roughened surface to promote bone integration or the surface may use a coating or be chemically etched to form a porous or roughened surface. In some embodiments the surface may include teeth. Each of the upper and lower endplates 102A-102D may use the same surface feature or different surface feature.

The expandable interbody spacer 100 components may be fabricated from any biocompatible material suitable for implantation in the human spine, such as metal including, but not limited to, titanium and its alloys, stainless steel, surgical grade plastics, plastic composites, ceramics, bone, or other suitable materials. In some embodiments, surfaces on the components may be formed of a porous material that participates in the growth of bone with the adjacent vertebral bodies. In some embodiments, the components may include a roughened surface that is coated with a porous material, such as a titanium coating, or the material is chemically etched to form pores that participate in the growth of bone with the adjacent vertebra. In some embodiments, only portions of the components be formed of a porous material, coated with a porous material, or chemically etched to form a porous surface, such as the upper and lower surfaces 144 that contact the adjacent vertebra are roughened or porous.

The expandable interbody spacer 100 may also be used with various tools, such as inserter tools, deployment tools and/or removal tools. The tools may include various attachment features to enable percutaneous insertion of the expandable interbody spacer 100 into the patient. For example, the tools may include arms or clamps to attach to the cutouts or other openings, slots or trenches of the drive mechanism. The tools may also include an actuation device to couple with the proximal section of the screw 108. Once the expandable interbody spacer 100 has been inserted and positioned within the intervertebral space between two vertebrae with the insertion tool, the deployment tool may actuate to deploy and expand the expandable interbody spacer 100 by applying a rotational force to screw 108.

In operation, the expandable interbody spacer 100 may be inserted into the intervertebral disc space between two vertebrae using an insertion tool. In some cases, the disc space may include a degenerated disc or other disorder that may require a partial or complete discectomy prior to insertion of the expandable interbody spacer 100. The deployment tool may engage with the proximal end of the expandable interbody spacer 100. As the deployment tool applies the rotational force, the expandable interbody spacer 100 gradually expands as described above. In some cases, the expandable interbody spacer 100 may need to be removed with a removal tool.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An expandable interbody spacer for placement between adjacent vertebrae comprising:
   two or more upper endplates, each endplate having two or more upper compound-angle linear rods extending from a bottom surface;
   two or more lower endplates, each endplate having two or more lower compound-angle linear rods extending from a top surface;
   a frame having multiple compound-angle bores configured to slidingly couple with at least one of upper and lower compound-angle linear rods of each upper and lower endplates;
   a housing having multiple compound-angle bores configured to slidingly couple with at least one of the upper and lower compound-angle linear rods of each the upper and lower endplates;
   wherein movement of the frame and housing toward each other slides the upper compound-angle linear rods and lower compound-angle linear rods outwardly from the compound-angle bores to move the upper and lower endplates simultaneously away from each other both vertically and horizontally to expand both a height and a width of the expandable interbody spacer from a collapsed state to an expanded state.

2. The expandable interbody spacer of claim 1, wherein movement of the frame and housing away from each other slides the upper compound-angle linear rods and lower compound-angle linear rods into the compound-angle bores to move the upper and lower endplates toward from each other both vertically and horizontally to reduce both the height and the width of the expandable interbody spacer and collapse the expandable interbody spacer to the collapsed state.

3. The expandable interbody spacer of claim 1, wherein vertically expands increases a vertical distance between the two or more upper and lower endplates, and horizontally expands increases a horizontal distance between the two or more upper endplates and a horizontal distance between the two or more lower endplates.

4. The expandable interbody spacer of claim 1, further comprising a drive screw coupled with the housing; and
   a threaded rod having a proximal end coupled with the drive screw and a distal end coupled to the frame;
   wherein movement of the drive screw in a first direction is configured to move the frame and housing toward each other, and movement of the drive screw in a second direction is configured to move the frame and housing away from each other.

5. The expandable interbody spacer of claim 1, wherein each upper and lower endplate includes distal compound-angle ramps configured to couple with corresponding compound-angle ramps on the frame, and each upper and lower endplate includes proximal compound-angle ramps configured to couple with corresponding compound-angle ramps on the housing.

6. An expandable interbody spacer for placement between adjacent vertebrae comprising:
   two or more upper endplates having a lower surface;
   two or more lower endplates having an upper surface,
   compound-angle linear rods coupled to the upper and lower surfaces;
   a frame having multiple compound-angle bores configured to slidingly couple with at least one compound-angle linear rod of each upper and lower endplate;
   a housing having multiple compound-angle bores configured to slidingly couple with at least one compound-angle linear rod of each the upper and lower endplate;
   wherein movement of the frame and housing toward each other slides the upper compound- angle linear rods and lower compound-angle linear rods outwardly from the compound-angle bores to move the upper and lower endplates simultaneously away from each other both vertically and horizontally to expand both a height and a width of the expandable interbody spacer from a collapsed state to an expanded state.

7. The expandable interbody spacer of claim 6, further comprising a drive screw coupled with the housing; and
   a threaded rod having a proximal end coupled with the drive screw and a distal end coupled to the frame;
   wherein movement of the drive screw in a first direction is configured to move the frame and housing toward each other, and movement of the drive screw in a second direction is configured to move the frame and housing away from each other.

8. The expandable interbody spacer of claim 6, wherein each upper and lower endplate includes distal compound-angle ramps configured to couple with corresponding compound-angle ramps on the frame, and each upper and lower endplate includes proximal compound-angle ramps configured to couple with corresponding compound-angle ramps on the housing.

9. The expandable interbody spacer of claim 6, wherein the compound-angle linear rods include at least one distal linear rod near a distal end of the bottom surface of each upper endplate and at least one proximal linear rod near a proximal end of the bottom surface each upper endplate, and the two or more lower compound-angle linear rods include at least one linear rod near a distal end of the top surface of each bottom endplate and at least one linear rod proximate a proximal end of the top surface of each bottom endplate.

10. The expandable interbody spacer of claim 6, wherein movement of the drive screw in a second direction is configured to move the frame and housing away from each other and collapse the expandable interbody spacer to the collapsed state.

11. The expandable interbody spacer of claim 6, wherein vertically expands increases a vertical distance between the two or more upper and lower endplates, and horizontally expands increases a horizontal distance between the two or more upper endplates and a horizontal distance between the two or more lower endplates.

12. An expandable interbody spacer for placement between adjacent vertebrae comprising:
   right and left upper endplates having compound-angle linear rods extending from a bottom surface;

right and left lower endplates having proximal and distal compound-angle linear rods extending from a top surface;
a frame having multiple compound-angle bores configured to slidingly couple with the proximal compound-angle linear rods of the right and left upper and lower endplates;
a housing having multiple compound-angle bores configured to slidingly couple with distal compound-angle linear rods of the right and left upper and lower endplates;
a drive screw coupled with the housing; and
a threaded rod having a proximal end coupled with the drive screw and a distal end coupled to the frame;
wherein movement of the drive screw in a first direction is configured to move the frame and housing toward each other and the compound-angle linear rods are configured to slide within the compound-angle bores to move the upper and lower endplates away from each other both vertically and horizontally to simultaneously expand both a height and a width of the expandable interbody spacer from a collapsed state to an expanded state.

13. The expandable interbody spacer of claim 12, wherein movement of the drive screw in a second direction is configured to move the frame and housing away from each other and collapse the expandable interbody spacer to the collapsed state.

14. The expandable interbody spacer of claim 12, wherein vertically expands increases a vertical distance between the right and left upper endplates and the right and left lower endplates, and horizontally expands increases a horizontal distance between the right upper and lower endplates and the left upper and lower endplates.

15. The expandable interbody spacer of claim 12, wherein each right and left upper endplate and each right and left lower endplate includes a distal compound-angle ramp configured to couple with a corresponding compound-angle ramp on the frame and a proximal compound-angle ramp configured to couple with corresponding compound-angle ramps on the housing.

16. The expandable interbody spacer of claim 12, wherein the compound-angle linear rods include at least one distal linear rod near a distal end of the bottom surface of each upper endplate and at least one proximal linear rod near a proximal end of the bottom surface each upper endplate, and the two or more lower compound-angle linear rods include at least one linear rod near a distal end of the top surface of each bottom endplate and at least one linear rod proximate a proximal end of the top surface of each bottom endplate.

* * * * *